United States Patent [19]
Kurnik et al.

[11] Patent Number: 5,827,183
[45] Date of Patent: Oct. 27, 1998

[54] METHOD OF MEASURING CHEMICAL CONCENTRATION IONTOPHORETICALLY USING IMPERMEABLE MASK

[75] Inventors: Ronald T. Kurnik, Foster City; Janet Tamada, Belmont; Michael Tierney, San Jose, all of Calif.

[73] Assignee: Cygnus, Inc., Redwood City, Calif.

[21] Appl. No.: 959,599

[22] Filed: Oct. 29, 1997

Related U.S. Application Data

[62] Division of Ser. No. 527,061, Sep. 12, 1995, Pat. No. 5,735,273.

[51] Int. Cl.⁶ ..................................................... A61N 1/30
[52] U.S. Cl. ........................... 600/345; 600/347; 604/20; 604/304
[58] Field of Search .............................. 604/20, 304–308; 600/345–348, 362, 365, 382, 307, 309, 386, 391, 395, 396, 397

[56] References Cited

U.S. PATENT DOCUMENTS

| | | | |
|---|---|---|---|
| 4,477,971 | 10/1984 | Jacobsen et al. | 29/877 |
| 4,595,011 | 6/1986 | Phillips . | |
| 4,633,879 | 1/1987 | Ong | 128/641 |
| 4,657,748 | 4/1987 | Lattin et al. | 604/20 |
| 4,702,732 | 10/1987 | Powers et al. | 604/20 |
| 4,722,726 | 2/1988 | Sunderson et al. | 604/20 |
| 4,722,761 | 2/1988 | Cartmell et al. | 156/242 |
| 4,731,049 | 3/1988 | Parsi | 604/20 |
| 4,732,155 | 3/1988 | Zetter et al. . | |
| 4,752,285 | 6/1988 | Petelenz et al. | 604/20 |
| 4,968,297 | 11/1990 | Jacobsen et al. | 604/20 |
| 5,003,987 | 4/1991 | Grinwald . | |
| 5,036,861 | 8/1991 | Sembrowich et al. | 128/763 |
| 5,037,380 | 8/1991 | Jacobsen et al. | 604/20 |
| 5,057,072 | 10/1991 | Phipps | 604/20 |
| 5,076,273 | 12/1991 | Schoendorfer et al. | 128/632 |
| 5,139,023 | 8/1992 | Stanley et al. | 128/637 |
| 5,140,985 | 8/1992 | Schroeder et al. | 128/632 |
| 5,250,022 | 10/1993 | Chien et al. | 604/20 |
| 5,279,563 | 1/1994 | Glikfeld et al. | 604/20 |
| 5,362,307 | 11/1994 | Guy et al. | 604/20 |

FOREIGN PATENT DOCUMENTS

| | | |
|---|---|---|
| A-228259 | 7/1987 | European Pat. Off. . |
| 0 304 304 | 2/1989 | European Pat. Off. . |
| A-453283 | 10/1991 | European Pat. Off. . |
| WO 92/07619 | 5/1992 | WIPO . |
| WO 92/10234 | 6/1992 | WIPO . |
| WO 93/00982 | 1/1993 | WIPO . |

OTHER PUBLICATIONS

Glikfeld, Peretz, et al., "Noninvasive Sampling of Biological Fluids by Iontophoresis", *Pharm Res.* (US), 1989, vol. 6, No. 11, pp. 988–990.

Meyerhoff et al., "On Line Continuous Monitoring of Subcutaneous Tissue Glucose in Men by Combining Portable Glucosensor with Microdialysis", *Diabetologia* (Germany), 1992, vol. 35, No. 11, pp. 1087–1092.

*Primary Examiner*—Jennifer Bahr
*Assistant Examiner*—Stephen Huang
*Attorney, Agent, or Firm*—Barbara G. McClung; Angela Horne; Bozicevic & Reed LLP

[57] ABSTRACT

A method for measuring the concentration of a chemical present in a blood stream of a mammalian subject is disclosed. The method involves contacting the subject's skin with a sensor assembly comprised of an ionically conducting material which contacts the skin, a working electrode which is in contact with the ionically conducting material which electrode has a catalytic surface and a mask having an opening therein. The mask is positioned between the skin and the working electrode. When the electrode is activated, chemical is transported through the skin and the ionically conductive material. The mask is positioned so that it blocks the flow into the catalytic surface except for flow which is substantially axially to the catalytic surface. Electrical signal generated at the working electrode is monitored over a period of time and correlated with a concentration of chemical present in the blood stream of the mammalian subject. The mask reduces or eliminates chemical signal which can radially transport toward the working electrode thereby reducing or eliminating edge effects making it possible to obtain a more accurate measurement.

13 Claims, 4 Drawing Sheets

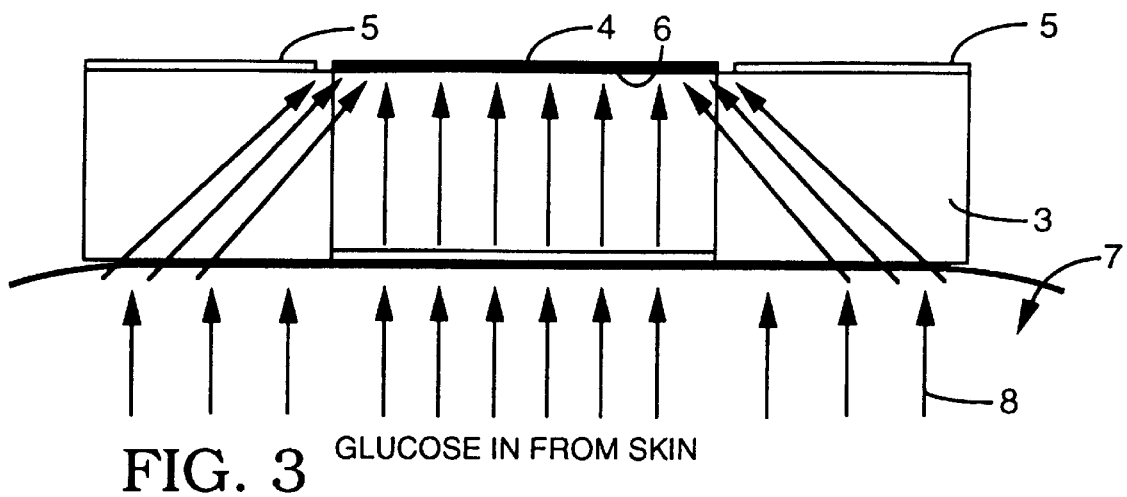
FIG. 3  GLUCOSE IN FROM SKIN
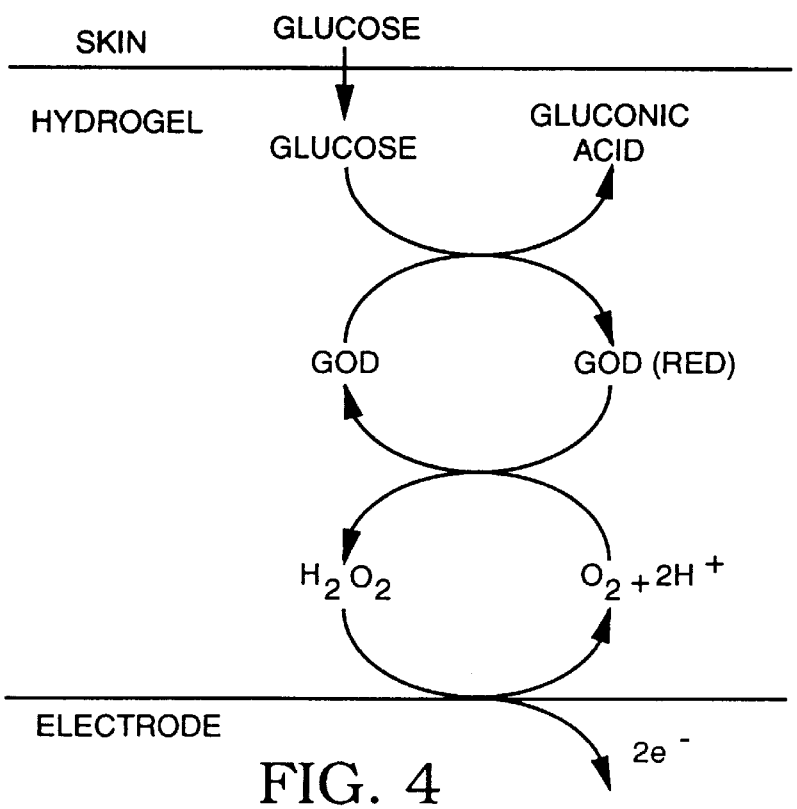
FIG. 4
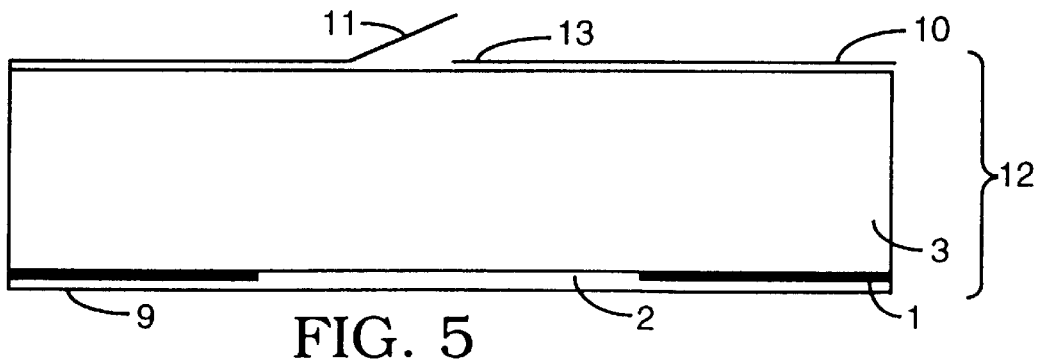
FIG. 5

METHOD OF MEASURING CHEMICAL CONCENTRATION IONTOPHORETICALLY USING IMPERMEABLE MASK

This application is a divisional application of U.S. application Ser. No. 08/527,061, filed Sep. 12, 1995 (now U.S. Pat. No. 5,735,273 issued Apr. 7, 1998) which application is incorporated herein by reference and to which application we claim priority under 35 USC §120.

FIELD OF THE INVENTION

This invention relates generally to the detection of chemical signals that are diffused through a solid or semi-solid, or quiescent liquid surface, particularly where the chemical signals are associated with a medically important molecule.

BACKGROUND OF THE INVENTION

An electrode is the component in the electrochemical cell in contact with an electrolyte through which current can flow by electronic movement. Electrodes, which are essential components of both galvanic (current producing) and electrolytic (current using) cells, can be composed of a number of electrically conductive materials, e.g., lead, zinc, aluminum, copper, iron, nickel, mercury, graphite, gold, or platinum. Examples of electrodes are found in electric cells, where they are dipped in the electrolyte; in medical devices, where the electrode is used to detect electrical impulses emitted by the heart or the brain; and in semiconductor devices, where they perform one or more of the functions of emitting, collecting, or controlling the movements of electrons and ions.

The electrolyte can be any substance that provides ionic conductivity, and through which electrochemically active species can be transported (e.g., by diffusion). Electrolytes can be solid, liquid, or semi-solid (e.g., in the form of a gel). Common electrolytes include sulfuric acid and sodium chloride, which ionize in solution. Electrolytes used in the medical field must have a pH which is sufficiently close to that of the tissue in contact with the electrode (e.g., skin) so as not to cause harm to the tissue over time.

Electrochemically active species that are present in the electrolyte can undergo electrochemical reactions (oxidation or reduction) at the surface of the electrode. The rate at which the electrochemical reactions take place is related to the reactivity of the species, the electrode material, the electrical potential applied to the electrode, and the efficiency at which the electrochemically active species is transported to the electrode surface.

In unstirred electrolyte, such as quiescent liquid solutions and gel electrolytes, diffusion is the main process of transport of electrochemically active species to the electrode surface. The exact nature of the diffusion process is determined by the geometry of the electrode (e.g., planar disk, cylindrical, or spherical), and the geometry of the electrolyte (e.g., semi-infinite large volume, thin disk of gel, etc.). For example, diffusion of electrochemically active species to a spherical electrode in a semi-infinite volume of electrolyte differs from diffusion of electrochemically active species to a planar disk electrode. A constant and predictable pattern of diffusion (i.e., a diffusion pattern that can be predicted by a simple equation) is critical in determining a correlation between the electrochemical current collected, and the concentration of the electrochemically active species in the electrolyte.

However, diffusion of electrochemically active species toward an electrode can not be predicted by a simple equation for every situation. For example, where the electrochemically active species diffuses through a disk-shaped electrolyte toward a smaller disk-shaped electrode in contact with the electrolyte, the current observed at the electrode can not be predicted by a simple equation. In this latter situation, the inaccuracy in the diffusion model is caused by the combination of two different diffusion models. First, in the center of the disk electrode the diffusion of the electroactive species towards the electrode is in a substantially perpendicular direction. Secondly, at the edges of the disk electrode the diffusion comes from both perpendicular and radial directions. The combination of these two different diffusion patterns makes the total current collected at the disk electrode difficult to predict. In addition, the relative contributions of the diffusion fluxes from the axial and radial directions may change over time, causing further errors in predicted current.

SUMMARY OF THE INVENTION

A mask which is substantially impermeable to the transport of a chemical signal is positioned in the chemical signal transport path moving toward a working electrode which senses an electrochemical signal diffused through a material which is ionically conductive, which material comprises water and an electrolyte. More particularly, the mask of the invention is positioned on or in the ionically conductive material, such as an ion-containing gel, between an area from which the chemical signal is transported and the catalytic face of the working electrode used to sense the chemical signal. The configuration of the mask (e.g., shape, thickness, mask component(s)) is such that the mask prevents substantially all chemical signal transport (from the chemical signal source) having a radial vector component relative to a plane of the mask and the catalytic face of the working electrode, thus allowing primarily only chemical signal transport (e.g., diffusion) that is substantially perpendicular to the place of the mask and the catalytic surface of the working electrode. The mask thus minimizes radial transport of the chemical signal to the working electrode and accumulation of chemical signal at the periphery of the working electrode. The mask thus significantly reduces or eliminates edge effects, since the chemical signal that reaches the electrode is primarily only that chemical signal that is transported in a direction substantially perpendicular to the catalytic face of the working electrode. Substantially all transport of chemical signal to the working electrode surface via a path which includes an radial vector component (i.e., is not a path substantially perpendicular to the working electrode catalytic surface) is prevented from occurring by the mask, since the mask blocks entry of potentially radially transported chemical signal at the source. By substantially reducing edge effects created by radial transport of chemical signal, it is possible to obtain a more accurate measurement of the amount (e.g., concentration) of chemical signal that is transported from a given area of source material.

In one embodiment, the working electrode is a closed polygon or closed circle. The mask has an outer perimeter which is equal to or greater than (i.e., extends beyond) the outer perimeter of the working electrode. The mask has an opening, the opening being sufficiently small so that chemical signal that passes through the opening to the catalytic surface of the working electrode in a direction that is substantially perpendicular to the plane of the mask, and thus, substantially perpendicular to the working electrode catalytic face.

In another embodiment, the working electrode is annular and the mask is composed of a solid, circular piece concentrically positioned with respect to the working electrode such that the outer perimeter of the solid circular piece is circumscribed substantially within the inner perimeter of the annular working electrode. Thus chemical signal that passes with the electrolyte flow and through the plane of the mask is substantially only that chemical signal that is transported from the chemical signal source in a direction that is substantially perpendicular to the working electrode catalytic face.

In another embodiment, the mask is attached to a surface of a hydrogel patch, and the mask and hydrogel patch are provided as a single unit.

In another embodiment, the mask is an integral part of the housing for the sensor portion of a device for monitoring the chemical signal.

In another embodiment, the mask is independent of any portion of the device with which it is to be used, i.e., the mask is not bound to another component but merely placed, by the user, in contact with the electrolyte containing material prior to use.

An object of the invention is to provide a means that can be used with virtually any surface-contacting working electrode, and can enhance the performance of the electrode and the accuracy of measurements from the working electrode.

Another object of the invention is to provide a means for accurately and consistently measuring the amount of a chemical signal present in a sample by minimizing the error created by chemical signal which moves to the electrode with a radial vector component.

Another object of the invention is to provide a means for quickly, accurately, and continually measuring a chemical signal transported through an electrolyte containing ion conducting material, e.g., a hydrogel. By using the mask of the invention with a working electrode as described herein, measurement of the chemical signal transported through the material in a path perpendicular to the electrode is achieved within a matter of seconds to minutes.

An object of the invention is to provide a disposable assembly which makes it possible to proportionally measure a chemical signal by conversion into an electrical signal, where the electrical signal can be measured and accurately correlated with the amount of chemical signal present in a given source (e.g., the amount of chemical signal present in and/or below a section of skin, or in a hydrogel patch in contact with the working electrode).

An advantage of the invention is that use of the mask with a working electrode and hydrogel allows for measurement of very small amounts of an electrochemical signal. For example, the mask of the invention can be used in conjunction with a working electrode, electroosmotic electrode and hydrogel system for monitoring glucose levels in a subject. An electroosmotic electrode (e.g., reverse iontophoresis electrode) can be used to electrically draw glucose into the hydrogel. Glucose oxidase (GOD) contained in the hydrogel catalyzes the conversion of glucose to generate a reaction product (hydrogen peroxide) which can be proportionally converted to an electrical signal. The electroosmotic electrode is switched off and the working electrode of the invention is turned on. The working electrode catalyzes the resulting chemical signal into an electrical signal which is correlated to the amount of chemical signal. This system allows for the continuous and accurate measurement of an inflow of a very small amount of glucose (e.g., glucose concentrations 10, 500, or 1,000 or more times less than the concentration of glucose in blood).

Another advantage is that the mask is easily and economically produced and is disposable.

A feature of the mask and the device used therewith is that it is flat (e.g., a disk with substantially planar surfaces), thin (e.g., 0.5 to 10 mils), impermeable to chemical signal flow with the electrode/mask/hydrogel assembly having a surface area on each face in the range of about 0.5 $cm^2$ to 10 $cm^2$.

A feature of the mask is that where the mask includes an opening, the opening has substantially the same dimensions or smaller as the working electrode i.e., the outer perimeter of the opening is circumscribed within the outer perimeter of the catalytic surface of the working electrode.

These and other objects, advantages and features of the present invention will become apparent to those persons skilled in the art upon reading the details of the composition, components and size of the invention as set forth below reference being made to the accompanying drawings forming a part hereof wherein like numbers refer to like components throughout.

BRIEF DESCRIPTION OF THE DRAWING

FIG. 3 is a cross-sectional view of an electroosmotic electrode/sensing electrode/hydrogel patch assembly without a mask according to the invention.

FIG. 4 is a schematic representation of the reaction which glucose oxidase (GOD) catalyzes to produce gluconic acid and hydrogen peroxide; hydrogen peroxide is then catalyzed at the working electrode into molecular oxygen, 2 hydrogen ions, and 2 electrons, the latter of which generates an electrical current.

FIG. 5 is a cross-sectional schematic view of a mask of the invention provided below a hydrogel patch.

DESCRIPTION OF THE PREFERRED EMBODIMENTS

Figure 1:
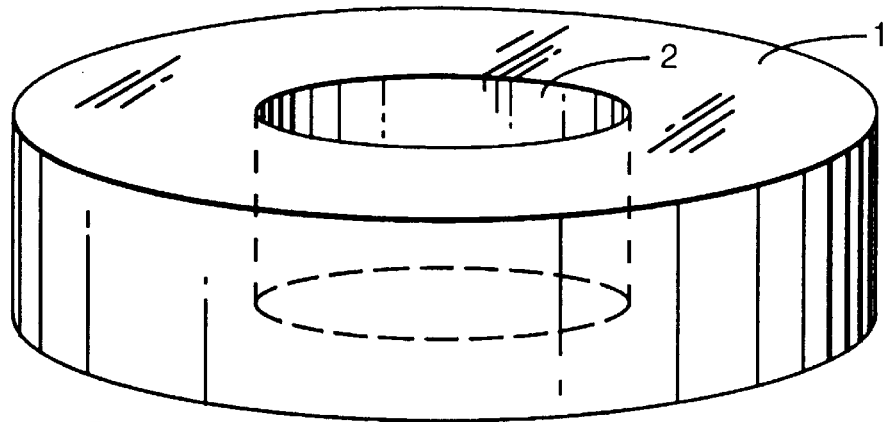
FIG. 1 is an overhead schematic view of a disc or donut shaped embodiment of the mask of the invention.

Before the mask of the present invention and assembly comprising such is described and disclosed it is to be understood that this invention is not limited to the particular components or composition described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the"

include plural referents unless the context clearly dictates otherwise. Thus, for example, reference to "a molecule" includes a plurality of molecules and different types of molecules.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described. All publications mentioned herein are incorporated herein by reference for the purpose of describing and disclosing the particular information for which the publication was cited in connection with.

Definitions

The term "mask," "impermeable mask," or "mask of the invention" means a thin (less than 50 mils, preferably 0.5 mil to 5 mils in thickness), substantially flat piece of material that, when positioned within the transport path of chemical signal moving toward a working electrode, reduces or prevents transport of chemical signal in a radial direction from the chemical signal source. The mask can be positioned on a face of the ionically conductive material, or can be positioned at any position within the ionically conductive material (e.g., such that the mask is contacted by material on each of its planar surfaces). In one exemplary configuration, the mask has an opening, which opening is substantially the same shape and size (e.g., smaller than or equal to) that of the working electrode. Thus, the outer perimeter of the opening is circumscribed substantially within the outer perimeter of the catalytic surface of the working electrode. When the opening is circular, the diameter is equal to or less than the diameter of the circular catalytic surface of a working electrode with which the mask is to used. In an alternative exemplary configuration, the mask is a solid piece of material (i.e., does not have an opening), and is used in conjunction with, for example, an annular working electrode. This type of mask is concentrically positioned with respect to the working electrode, so that chemical signal does not enter the region substantially concentric to the annular working electrode. The mask is composed of a material that is substantially impermeable to the flow of chemical signal that is to be detected. The mask and/or the mask opening are of a size sufficient to allow a detectable amount of chemical signal to reach the working electrode, while reducing or preventing entry of chemical signal into the electrolyte flow path that has a potential to be transported (eg., by diffusion) in a radial direction toward an edge of the working electrode. Thus, the mask substantially eliminates "edge effect" flow, i.e., the chemical signal impermeable mask area prevents chemical signal from contacting the electrode unless the signal flows substantially perpendicular to the surface of the working electrode.

The term "working electrode" means an electrode that detects a chemical signal by catalyzing the conversion of a chemical compound into an electrical signal (e.g., conversion of hydrogen peroxide into 2 electrons, molecular oxygen, and 2 hydrogen ions).

The term "catalytic surface" or "catalytic face" means the surface of the working electrode that: 1) is in contact with the surface of an ionically conductive material which comprises an electrolyte and allows for the flow of chemical signal; 2) is composed of a catalytic material (e.g., carbon, platinum, palladium, nobel metal, or nickel and/or oxides and dioxides of any of these); and 3) catalyzes the conversion of the chemical signal into an electrical signal (i.e., an electrical current) that is monitored and correlated with an amount of chemical signal present at the electrode.

"Chemical signal," "electrochemical signal," or "electrochemically active compound" means the chemical compound that is ultimately converted to an electrical signal and measured by the working electrode in conjunction with a monitoring device. Chemical signal which moves toward the working electrode at an angle, i.e., includes a radial vector component, is blocked by the mask. "Chemical signals" can be: 1) directly converted into an electrical signal by chemical reaction at the catalytic face of the electrode; or 2) indirectly converted into an electrical signal by the action of one or more catalysts. For example, the chemical signal glucose is indirectly converted into an electrical signal by reactions driven by two catalysts. A first catalyst, the enzyme glucose oxidase (GOD), converts glucose into gluconic acid and hydrogen peroxide. Hydrogen peroxide is then converted to an electrical signal by a second catalyst which second catalyst is the catalytic material (e.g., metal or metal oxide on the catalytic face of the working electrode.

"Ionically conductive material" means a material that provides ionic conductivity, and through which electrochemically active species can be transported (e.g., by diffusion). The ionically conductive material can be, for example, a solid, liquid, or semi-solid (e.g., in the form of a gel) material that contains an electrolyte, which can be composed primarily of water and ions (e.g., sodium chloride). Generally, the material comprises water at 50% or more by weight of the total material weight. The material can be in the form of a gel, a sponge or pad (e.g., soaked with an electrolytic solution), or any other material that can contain an electrolyte and allow passage of electrochemically active species, especially the chemical signal of interest, through it. An exemplary ionically conductive material in the form of a hydrogel is described in copending U.S. application Ser. No. 08/501,664, filed Jul. 12, 1995, incorporated herein by reference.

A "chemical signal target area" is an area on a surface of an ionically conductive material toward which chemical signal transport is desired. The chemical signal target area is generally an area of the ionically conductive material that, during chemical signal monitoring, is in contact with a chemical signal sensing means (e.g., a catalytic face of a working electrode), and is of the same size and shape as the portion of the chemical signal sensing means in contact with the ionically conductive material surface (e.g., the same size and shape as the catalytic face of the working electrode). For example, where the chemical sensing means to be used with the tonically conductive material is a circular working electrode, the chemical signal target area is a circular area of the ionically conductive material face that contacts the catalytic surface of the circular working electrode during chemical signal monitoring. In another example, where the chemical sensing means to be used with the ionically conductive material is an annular working electrode, the chemical signal target area is an annular area of the ionically conductive material face that contacts the catalytic surface of the circular working electrode during chemical signal monitoring.

Mask (General)

The invention must provide some basic characteristics in order to be useful for its intended purpose, which is to inhibit contact between a working electrode and radially inward transported chemical signal, particularly the form of the chemical signal that can be catalyzed into an electrical signal at the catalytic surface of the electrode (e.g., hydrogen peroxide that results from conversion of the chemical signal glucose).

For example, the mask of the invention can be used in connection with any metabolite monitoring device, where the device contains a working electrode that detects a chemical signal that is transported from one area (e.g., the skin and tissues below the skin) through an ion conducting material (e.g., a hydrogel) to the electrode surface. Examples of such devices include those described in PCT application serial no. PCT/GB93/00982 (incorporated herein by reference). Further exemplary devices, hydrogels, and additional components for use with the present invention are described in copending U.S. application Ser. No. 08/501,664, filed Jul. 12, 1995; and in copending U.S. application entitled "Electrode," filed on Sep. 11, 1995 as attorney docket no. 07498/003001; each of which applications are herein incorporated by reference in their entirety and which applications disclose inventions which were invented under an obligation to assign rights to the same entity to which the rights in the present invention were invented under an obligation to assign.

An exemplary ionically conductive material suitable for use with the invention is a hydrogel composed of a hydrophilic compound, water, and a salt. The hydrophilic compound forms a gel in the presence of water, and is generally present in the gel in an amount of about 4% or more by weight based on the total gel weight. The gel contains water in an amount of about 95% or less based on the weight of the hydrogel. The salt can be any salt that ionizes readily in water and facilitates electric conductivity through the gel, preferably a chloride containing salt (e.g., NaCl, KCl, etc.).

Regardless of the composition of the ionically conductive material, one face of the material has a chemical signal target area. The target area is the area on a face of the material toward which chemical signal transport is desired, e.g., the area of the material face that will be in contact with the catalytic face of a working electrode during chemical signal sensing. Preferably, the target area of the ionically conductive material is used with a working electrode that has a catalytic face having approximately the same shape and size as the target area (e.g., circular, annular, etc.). During monitoring, the mask is positioned on a second ionically conductive material face opposite the first material face having the target area, such that chemical signal that diffuses from the chemical signal source, through a plane of the mask, through the ionically conductive material, and toward the chemical signal target area is substantially only that chemical signal that is transported in a direction substantially perpendicular to the chemical signal target area.

An exemplary monitoring device that can be used in connection with the mask of the invention is generally composed of: 1) a hydrogel patch, one face of which is contacted with a source of biologically important molecules such as the skin of a mammalian subject; 2) an electroosmotic electrode which is positioned on the face of the hydrogel patch opposite the face in contact with the mammalian subject's skin; 3) a working electrode having a catalytic material on at least its catalytic face, the catalytic face of the electrode being that face in contact with the same face of the hydrogel as the electroosmotic electrode; 4) a means for generating an electrical current through the electroosmotic electrode, the electrical current serving to electrically draw molecules through the mammalian subject's skin, into the hydrogel patch, and toward the catalytic face of the working electrode; and 5) a monitoring means for monitoring electrical current generated at the catalytic face of the working electrode. Alternatively, the chemical signal can enter the hydrogel by passive diffusion, i.e., the assembly can be used without an electroosmotic electrode.

Such a monitoring device can be used to monitor levels of a metabolically important compound in, for example, the bloodstream of a mammalian subject (e.g., a human subject). As used herein, the metabolic compound in this example is termed the "chemical signal." For example, the metabolic compound (and chemical signal) can be glucose. That chemical signal is converted to a useful chemical signal and then converted to an electrical signal as shown in FIG. 4. The electroosmotic electrodes are used to electrically draw glucose molecules through the mammalian subject's skin, into the hydrogel, and toward the catalytic face of the working electrode. The hydrogel contains the enzyme glucose oxidase (GOD), which converts the glucose into gluconic acid and hydrogen peroxide. The hydrogen peroxide is then converted into molecular oxygen, 2 hydrogen ions and 2 electrons, the latter of which generates an electrical current in the working electrode (see FIG. 4). The electrical current is measured by the attached monitoring device, and correlated with the amount of glucose present in the subject's bloodstream.

An assembly of the invention comprised of an electrode and mask positioned on either side of a hydrogel is used with a monitoring device as described above by positioning the mask between mammalian subject's skin and the face of the hydrogel in contact with the subject's skin, such that chemical signal that diffuses from the subject's skin and past the plane of the mask is only that chemical signal that is transported in a path substantially perpendicular to the catalytic face of the working electrode. It is important that the mask does not completely occlude contact of the ionically conductive material (e.g., the hydrogel) with the chemical signal source (e.g., the subject's skin).

Figure 2A:
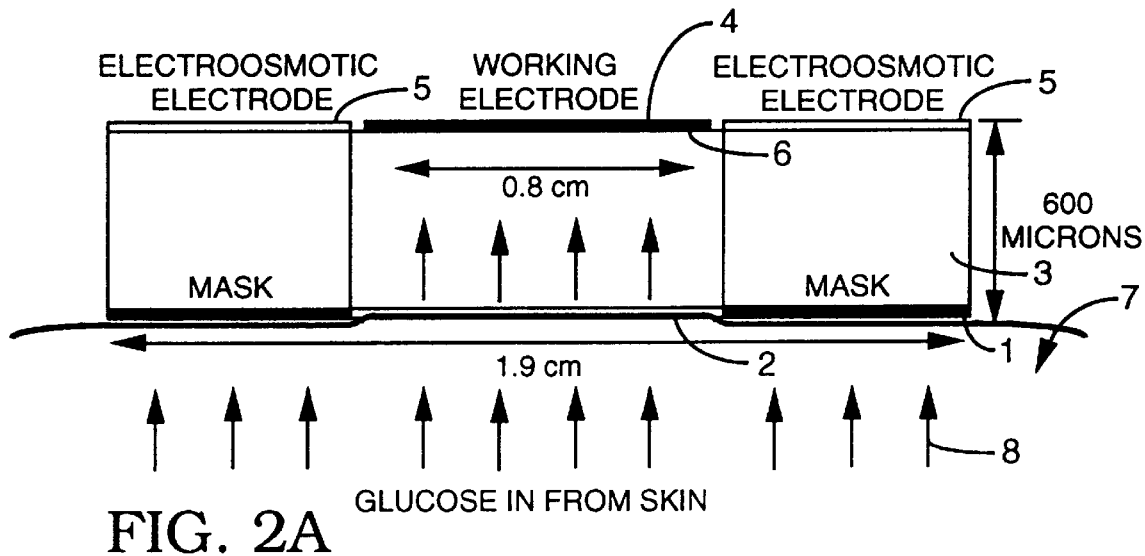
FIGS. 2A and 2B are cross-sectional views of embodiments of an electroosmotic electrode/working electrode/hydrogel patch assembly with a mask according to the invention.
Figure 2B:
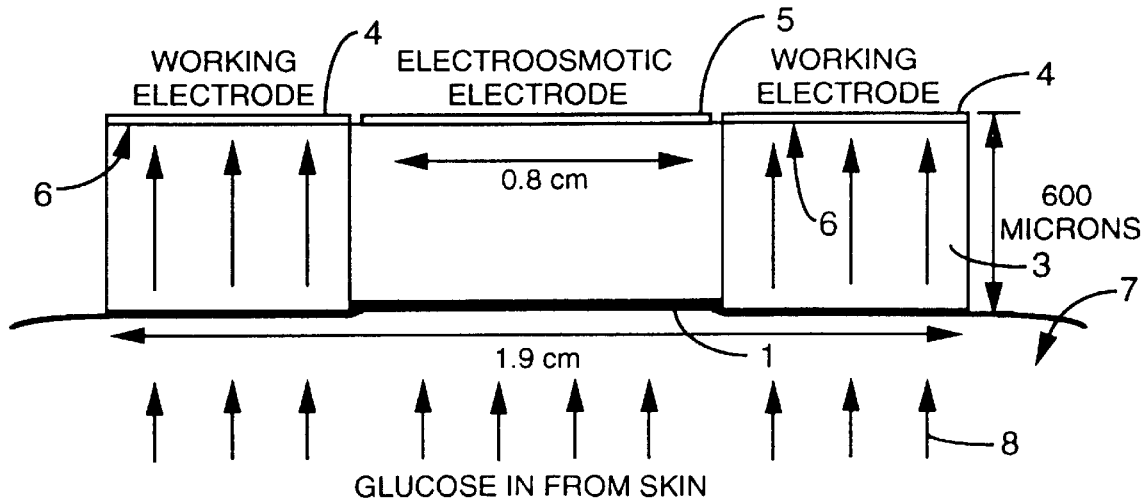

An exemplary assembly of the invention is shown in FIG. 2A, where the working electrode 4 and mask 1 are circular, and the mask has an opening 2 that is positioned so that it is directly beneath the working electrode 4 on the opposite face of the gel 3. Because the mask is impermeable to the chemical signal (e.g., glucose), chemical signal is electrically drawn via a substantially perpendicular path only through the opening in the mask. An additional exemplary assembly of the invention is shown in FIG. 2B, where the working electrode is annular (circular with a circular opening in the center), and the mask 1 is a solid, circular piece positioned concentric to the working electrode such that the outer perimeter of the mask 1 is substantially circumscribed within the inner perimeter of the annular working electrode 4. In this embodiment, the annular working electrode extends from approximately the outer perimeter of the mask to the outer perimeter of the ionically conductive material (e.g., hydrogel) used in conjunction with the mask 1 and working electrode 4. For example, where the radius of the a circular hydrogel is 0.95 cm, the radius of the mask can be about 0.5 cm and the width of the working electrode is about 0.45 cm.

The position of the mask, and the inhibition of the entry of glucose into gel areas other than that directly beneath the working electrode minimizes the radial component of chemical signal transport. Reduction of radial transport of the chemical signal toward the working electrode reduces accumulation of such radially transported compound at the periphery of the electrode, thereby reducing the edge effects associated with this phenomenon. It is recognized that the mask can allow for a small amount of radial chemical signal transport from the chemical signal source toward the working electrode where, for example, the error in measured electrical current associated with electrochemical conversion of the radially transported chemical signal is of a magnitude that does not significantly affect the accuracy of the measurement of the amount of chemical signal (e.g., the concentration of chemical signal in a subject's bloodstream). Thus, for example, where the mask has an opening, the opening can be slightly larger than the diameter of the working electrode used in conjunction with the mask.

The (1) size or geometric surface area of the working electrode, (2) thickness of the gel, (3) size of the opening in the mask, and (4) width of the mask surrounding the opening are all interrelated to each other. For example, when the thickness of the gel is increased the size of the opening must be decreased to obtain the same degree of elimination of radially transported chemical signal. The smaller the opening in the mask the greater the ability to block radial transport of chemical signal. Although it is desirable to decrease radial transport of the chemical signal, it is also desirable to maximize the chemical signal received and the chemical signal is decreased by a smaller opening in the mask.

For reasons that may relate to factors such as the build up of undesired materials, components such as the hydrogel, mask and the electrodes must be easily replaceable by a patient in a convenient manner. Accordingly, an assembly of these components must have some structural integrity, and provide for the detection of the chemical signal of interest. In that the device is preferably small (e.g., hand held, e.g., the size of a watch to be worn on the wrist of a patient), it is necessary that the assembly of components be particularly thin. The mask generally has a thickness of about 0.5 to 10 mils (1 mil equals one thousandth of an inch) and the hydrogel has a thickness in the range of about 5 mils to 60 mils, generally about 10 mils to 60 mils, normally about 600 microns (about 24 mils).

In order to accurately measure the amount of a chemical signal (e.g., the amount of hydrogen peroxide generated by GOD catalysis of glucose) and be sufficiently large to be manipulated, the device cannot be too thin and cannot be too small. The overall surface area of the hydrogel on a single surface should be in the range of about 0.25 $cm^2$ to about 10 $cm^2$, preferably about 0.50 $cm^2$ to 5 $cm^2$. The electrodes of the entire monitoring device, which include both electroosmotic and working electrodes, must have a total surface area that is less than that of the hydrogel patch. In general, the surface area of a mask (the area of the mask, and the opening where applicable) suitable for use in the monitoring device ranges from about 0.1 $cm^2$ to about 6 $cm^2$, preferably about 0.25 $cm^2$ to 2.0 $cm^2$, more preferably about 1.0 $cm^2$.

Basic Structure

FIG. 1 is an overhead schematic view of an exemplary mask of the invention. The mask may be any configuration but is preferably donut shaped as per FIG. 1, with an outer perimeter that is equal to or larger than that of the working electrode and/or is substantially the same as the hydrogel patch used in conjunction with the mask. The mask opening is generally equal in size to about 50% of the area of the working electrode ±20%. In general, the mask opening constitutes an area that is in the range of 1% to 90% of the area encompassed by the mask plus the opening. The mask 1 is disc-shaped, and has a diameter equal to or less than the diameter of the hydrogel patch used in conjunction with the mask, the diameter being in the general range of about 0.5 cm to 3.0 cm, generally about 1.9 cm. In general, the range of the surface area of the hydrogel patch used in conjunction with the mask is from about 0.5 $cm^2$ to about 10 $cm^2$, preferably in the range of about 1 $cm^2$ to about 5 $cm^2$. The mask 1 defines an opening 2 positioned substantially in the center of the mask 1. The diameter of opening 2 is less than or equal to the diameter of the catalytic surface of the working electrode that is to be used in conjunction with the mask, generally in the range of about 0.4 cm. Normally, the mask opening constitutes an area that is about 5/815% of the total area encompassed by the catalytic face of the working electrode, equal to, or slightly larger than the catalytic face of the working electrode (e.g., 100.5% to 105% of the catalytic surface area).

Alternatively, the mask can be a composed of a solid, circular piece for use with, for example, an annular working electrode. The solid, circular mask is concentrically positioned with respect to an annular working electrode such that the outer perimeter of the solid circular piece is circumscribed substantially within the inner perimeter of the annular working electrode. Thus chemical signal that diffuses from the chemical signal source and through the mask(s) is substantially only that chemical signal that diffuses from the chemical signal source in a direction that is substantially perpendicular to the plane of the mask, and thus, substantially perpendicular to the annular working electrode catalytic face.

The mask is preferably thin, generally having a thickness in the range of about 0.01 mil to 10 mils, normally about 0.5 mil to 5 mils (1 mil equals one-thousandth of an inch). The working electrode used in conjunction with the mask of the invention generally has a geometric surface about 5% to 90%, preferably about 10% to 80% of the geometric surface of the hydrogel.

The mask is composed of a material that is substantially impermeable to the chemical signal to be detected (e.g., glucose), and can be permeable to substances other than the chemical signal of interest. By "substantially impermeable" is meant that the mask material reduces or eliminates chemical signal transport (e.g., by diffusion). The mask can allow for a low level of chemical signal transport, with the proviso that chemical signal that passes through the material of the mask does not cause significant edge effects at the working electrode use in conjunction with the mask. Examples of materials that can be used to form the impermeable mask include mylar, polyethylene, nylon and various other synthetic polymeric material. The mask can be composed of a single material, or can be composed of two or more materials (e.g., the mask is composed of multiple layers of the same or different materials) to form a chemical signal-impermeable composition.

In general, the size of the mask (i.e., diameter, surface area, thickness, etc.), the geometry of the mask (e.g., circular, oval, annular, polygonal, etc.), the size (e.g., diameter, surface area, etc.) and/or geometry (e.g., annular, circular, oval, polygonal) of a mask opening through which the chemical signal is to be detected, compositions of the mask (e.g., type and number of materials, number of layers, chemical signal to which the mask is permeable), the number of mask used in an assembly of the invention (i.e., the number and position of the masks in the electrolyte flow path between the catalytic surface of the working electrode and the chemical signal source) and other characteristics of the mask will vary according to a variety of factors such as, for example, the diameter of the hydrogel patch, the diameter of the working electrode, the diameter of the electroosmotic/working electrode assembly, the chemical signal to be detected, the characteristics of the chemical signal's path of transport (e.g., the diffusion characteristics of the chemical signal), and the geometry and size of the monitoring device.

Methods for making the mask include die cutting and stamping according to methods well known in the art. Most preferably, the mask is manufactured in a manner that is the most economical without compromising performance of the mask (e.g, the impermeability of the mask to the chemical signal of interest, the ability to manipulate the mask by hand without breaking or otherwise compromising its operability). The mask may have an adhesive including a pressure sensitive adhesive coated on one or both surfaces. Further, the mask may be coated with a material which absorbs one or more compounds or ions flowing in the hydrogel.

Configurations

The mask can be supplied in several different configurations. Examples of these configurations include: 1) the mask supplied in connection with a hydrogel patch; 2) the mask supplied as an integral component of a monitoring device; or 3) the mask supplied as an independent component.

FIG. 5 illustrates how the mask of the invention can be supplied with a hydrogel patch as a hydrogel/mask assembly 12. The mask 1 is positioned on one face of the gel 3. The mask can be attached to the gel 3 by any suitable chemical means (e.g., adhesive) that do not affect the impermeability of the mask to the chemical signal of interest or the conductivity of the gel for electrically-induced movement of the chemical signal through the mask opening and into and through the hydrogel. Release liner components 9 and 10 are positioned on opposite surfaces of the assembly 12 to provide improved handleability of the assembly 12 in that the assembly 12 may be slightly fragile (e.g., may tear during shipping or repeated handling) and/or wet and sticky. The release liner 10 may include a perforated cut (e.g., an S-shaped cut) or may include two portions 11 and 13 that overlap one another to allow easy removal of the release liner 10. Prior to use, the release liners 9 and 10 are removed from the assembly 12, and the assembly 12 positioned in the sensor housing of a monitoring device so that the mask will be in contact with the subject's skin, and the hydrogel will be in contact with the electroosmotic and working electrodes.

Figure 6:
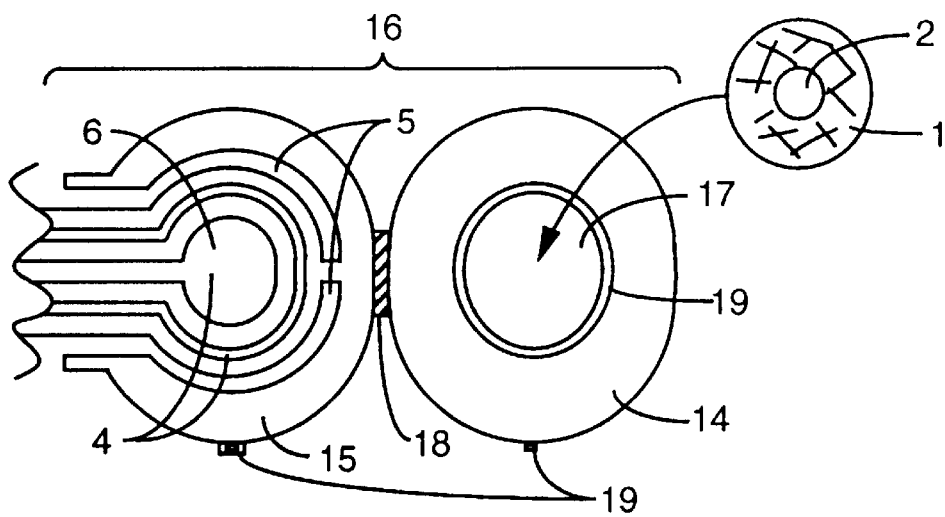
FIG. 6 is an overhead schematic view of a sensor housing containing electroosmotic and working electrodes and a mask.

In another embodiment, the mask is an integral component of the sensor housing of a monitoring device. An example of a sensor housing of a monitoring device is illustrated in FIG. 6. The sensor housing 16 of the monitoring device includes a top portion 15 containing electroosmotic 5 and working 4 electrodes, and a bottom portion 14 defining an opening 17, the opening having a diameter at least slightly less than that of the mask 1 so that the mask fits tightly in the recess 19. The top portion 15 and the bottom portion 14 can be connected by a hinge 18 that permits opening and closing of the sensor housing. The mask 1 is either permanently or removably fitted over this sensor housing opening 17. The edges of the sensor housing opening 17 can define a recess 19 so as to easily receive the mask 1 and seat the mask 1 within the recess 19. The mask can be secured into position in the bottom portion 14 of the sensor housing 16 by any suitable chemical means (e.g., adhesive) or physical means (e.g., physically attaching the mask to the opening by melting the edges of the mask 1 edges to the edges of the opening 17), provides that the operability of the mask, the hydrogel, the sensor housing, and/or the monitoring device are not significantly affected.

The entire assembly is used by inserting a hydrogel patch (as per the gel 3 of FIG. 5) over the mask 1 in the bottom portion 14, and bringing the top portion 15 into position over the bottom portion 14 so that the electroosmotic electrode 5 and working electrodes 4 contact the central portion of the hydrogel. The top portion 15 and the bottom portion 14 can be held together by interconnecting portions of a securing means 19 (e.g., a latch) which can be closed and opened repeatedly, preferably for the life of the sensor housing. The bottom portion 14 is then positioned on the subject's skin so that the hydrogel contained within the bottom portion 14 is in contact with the skin through opening 2. When properly aligned, the opening 2 in the mask 1 is positioned beneath the approximate center of the catalytic face 6 of the working electrode 4, so that chemical signal that is transported axially through the hydrogel accessible through the mask opening 2 and will come in contact with the central portion of the catalytic face 6 of the working electrode 4.

In another embodiment, the mask is supplied as an independent component, e.g. for insertion into a sensor housing as exemplified in FIG. 6. The mask is inserted in the device prior to use as described above and in FIG. 6, the hydrogel inserted within the bottom portion of the sensor housing and on top of the mask, and the device assembled as described above.

Regardless of the embodiment used, all of the masks of the invention: 1) are impermeable to the chemical signal to be detected; 2) have a diameter that is at least the same or greater than the diameter of the hydrogel patch used in conjunction with the mask; and either 3) are configured for use with a working electrode so that when positioned in the path of electrolyte flow from the chemical signal source, substantially only chemical signal that flows from the source in a direction substantially perpendicular to the working electrode is allowed to enter the electrolyte flow path.

The mask is generally used in conjunction with an electroosmotic electrode (e.g., an iontophoresis or reverse iontophoresis electrode). An electroosmotic electrode suitable for use with the invention is described in copending U.S. application Ser. No. 08/2265,844, filed Jun. 24, 1995 (which application is incorporated herein by reference in its entirety, and which discloses an invention invented under an obligation to assign to the same entity as that to which the rights in the present application are assigned).

The electroosmotic electrode is used to create an electrical field which transports material such as ions and non-polar molecules from one area (e.g., skin, blood and flesh) to the area of the working electrode. It is important the electroosmotic electrode and the working electrode be used alternately (i.e., current is present in the electroosmotic electrode or the electrical current generated at the working electrode is measured—not both at once).

Working electrodes suitable for use with the invention include any electrode having a catalytic surface for detection of a chemical signal. An example of a suitable working electrode is described in copending U.S. application entitled "Electrode," filed on Sep. 11, 1995 as attorney docket no. 07498/003001, incorporated herein by reference. A standard bipotentiostat circuit can be used to bias the working and scavenging electrodes independently versus the reference electrode.

Based on the description above and in the figures, it will be recognized that the working electrode of the invention can be configured in a variety of different forms, and from a variety of different materials. The mask will change with the working electrode so as to maintain certain defined mechanical, electrical, chemical and transport (e.g., diffusion) characteristics.

Mechanically the mask will have sufficient structural integrity such that it can be readily handled by human fingers without significant handling difficulties or significantly compromising the performance of the mask. Preferably, the mask will be somewhat flexible so that it can bend at least slightly during handling without creasing, breaking, or being otherwise compromised in, for example, its impermeability to the chemical signal of interest. The relative mechanical requirements of the mask may vary with the particular mask embodiment. For example, where the mask is an integral part of the sensor housing, it may be desirable to design the mask so that it can be separated from the patch without significantly tearing the patch, or adhering to the patch in a manner that makes it difficult to completely remove all patch material from the face of the mask.

The mask must maintain its impermeability to the chemical signal of interest. Preferably, the mask will optimally function at a pH which is relatively close to that from which the chemical signal is withdrawn (e.g, human skin (about 7)) and at least within a range of from about pH 4 to pH 9.

Utility

The present invention is useful in connection with the detection of biologically significant molecules such as glucose which is moved through human skin using a technique known as electroosmosis. The basic concept of moving a molecule such as a glucose through human skin is disclosed within U.S. Pat. No. 5,362,307, issued Nov. 8, 1994 and U.S. Pat. No. 5,279,543, issued Jan. 18, 1994 which patents are incorporated herein by reference for disclosing the basic concept of moving molecules such as glucose through human skin by means of electroosmosis. The concept of converting the very small amounts of molecules such as glucose which can be extracted through the skin in order to create a current by use of glucose oxidase is disclosed within earlier filed application Ser. No. 08/265,084, filed Jun. 24, 1994 and application Ser. No. 08/373,931, filed Jan. 10, 1995; hydrogel patches and working electrodes suitable for use with the present invention are disclosed within copending U.S. application Ser. No. 08/501,664, filed Jul. 12, 1995; and copending U.S. application entitled "Electrode," filed on Sep. 11, 1995 as attorney docket no. 07498/003001; each of which applications are incorporated herein by reference in their entirety and which applications disclose inventions which were invented under an obligation to assign rights to the same entity to which the rights in the present invention were invented under an obligation to assign.

FIG. 2A illustrates how an exemplary mask of the invention is used in conjunction with a hydrogel/electroosmotic electrode/working electrode system, such as that used in a metabolite monitoring device (e.g., a glucose monitoring device). The mask 1 is positioned on a face of the gel 3 with the opening 2 substantially in the center of the gel 3. A working electrode 4 and electroosmosis electrode 5 are positioned on the face of the gel 3 opposing the mask 1. The catalytic surface 6 of the working electrode 4 is positioned on the gel 3 so that the working electrode 4 is directly opposite the opening 2 of the mask 1. The face of the gel 3 attached to the mask 1 is placed on the surface 7 through which the chemical signal is to be diffused (e.g., mammalian skin, e.g., human skin).

During use in monitoring levels of a chemical signal of interest (e.g., glucose), an electrical current is sent through the electroosmotic electrode, thereby drawing molecules through the patient's skin and into the hydrogel patch. The mask permits entry of the chemical signal into the gel only at the opening 2, thus reducing the amount of chemical signal that is radially transported into the patch, as well as the amount of chemical signal that is capable of being transported radially toward the working electrode. The mask creates a column-like flow through the gel to the working electrode and substantially prevents any material from flowing to the electrode if that material includes a radial vector as a component of its movement, i.e., the material must move axially or perpendicular to the working electrode. The chemical signal permitted into the patch by entry through the opening in the mask is transported in a substantially axial direction toward the catalytic surface 6 of the working electrode 4, where it is converted to an electrical signal. Alternatively, the chemical signal is converted into an intermediate compound by a component in the gel 3. The intermediate compound in turn is transported to the catalytic surface 6 of the working electrode 4, where it is converted into an electrical signal. The electrical signal is detected by switching off the electroosmotic electrode, and monitoring the electrical current generated at the working electrode.

The use of the mask and advantages associated therewith are further illustrated by comparing the flow of glucose in a monitoring system either with (FIGS. 2A and 2B) or without (FIG. 3) the mask of the invention. FIG. 3 illustrates an electroosmotic electrode/working electrode/hydrogel patch assembly (without a mask of the invention) for monitoring glucose levels in a mammalian subject (e.g., a human subject). As described above, the electroosmotic electrodes (e.g., iontophoresis electrodes) 5 are activated to electrically draw glucose 8 through the subject's skin 7 and into the hydrogel 3. The iontophoresis electrode 5 is used to electrically draw glucose 8 through the subject's skin 7 and into the hydrogel 3. Glucose 8 is permitted to enter the gel 3 over the entire face of the gel 3 in contact with the subject's skin 7. As a result, glucose is present throughout the entire gel 3, rather than in a region substantially perpendicular to the catalytic face 6 of the working electrode 4. The gel 3 contains the enzyme glucose oxidase (GOD), which converts the glucose to hydrogen peroxide and gluconic acid. The conversion of glucose to hydrogen peroxide by GOD is illustrated schematically in FIG. 3. The hydrogen peroxide is transported (e.g., by diffusion) toward the catalytic face 6 of the working electrode 4, where it is converted into molecular oxygen, 2 hydrogen ions, and 2 electrons, the latter of which provides an electrical signal.

Because glucose is present throughout the entire gel 3, the hydrogen peroxide resulting from enzymatic conversion of glucose is also present throughout the entire gel 3. Because the surface area of the gel is greater than that of the working electrode, uncatalyzed hydrogen peroxide accumulates at the working electrode 4 periphery due to radial transport of the compound toward the catalytic surface 6. Accumulation of peroxide at the working electrode periphery produces a variable hydrogen peroxide flux (i.e., the amount of peroxide present over the working electrode at a given time is not directly correlated with the actual peroxide flux through the hydrogel), and thus produces a flux or error in the measured electrical current at the working electrode.

In contrast, and as illustrated in FIGS. 2A and 2B, the mask 1 of the invention permits entry of glucose 8 only at the opening 2 (in FIG. 2A) or the non-mask contacting portion of the gel 3 (as in FIGS. 2A and 2B). The opening and/or non-mask contacting gel surface is directly opposite the catalytic surface 6 of the working electrode 4. The glucose 8 is converted into hydrogen peroxide and gluconic acid by GOD, which is contained in the gel 3. The hydrogen peroxide produced is generally positioned within the gel in a region that is beneath and substantially perpendicular to the catalytic face 6 of the working electrode 4. Thus, the radial transport component of hydrogen peroxide illustrated in FIG. 3 is eliminated, and an increased flux or error in current measured at the working electrode 4 periphery does not occur.

The composition, size and thickness of the mask and other components can be varied and such variance can affect the time over which the components can be used. For example, the hydrogel patches may be connected to the mask and are generally designed to provide utility over a period of about 24 hours. After that time some deterioration in characteristics, sensitivity, and accuracy of the measurements from the electrode can be expected (e.g., due to reduced effectiveness of an enzyme in the hydrogel). Due to other problems the working electrode and hydrogel patch, preferably the entire device, should be replaced. The invention contemplates components, assemblies and devices which are used over a shorter period of time e.g., 8 to 12 hours or a longer period of time e.g., 1 to 30 days.

In its broader sense, a mask of the invention can be used to carry out a method which comprises extracting any biomedically significant substance through the skin of a human patient and reacting that substance with another substance or substances (which reaction is greatly accelerated by the use of an enzyme e.g., 10 to 100 times or more as fast) to form a product which is detectable electrochemically by the production of a signal which signal is generated proportionally based on the amount of a biologically important or biomedically significant substance drawn into the patch. As indicated in the above-cited patents the ability to withdraw biochemically significant substances such as glucose through skin has been established (see U.S. Pat. Nos. 5,362,307 and 5,279,543). However, the amount of compound withdrawn is often so small that it is not possible to make meaningful use of such methodology in that the withdrawn material cannot be precisely measured and related to any standard.

Moreover, conventional hydrogel/working electrode assemblies are severely compromised in their ability to accurately, quickly, and continuously monitor levels of the chemical signal. As described above, in devices without a mask chemical signal is radially transported toward the catalytic surface of the working electrode and accumulates at the working electrode periphery, thus causing the flux or error of chemical signal to be greater at the electrode edges than at the electrode center, a phenomenon termed "edge effects." The edge effects result in varying electrical signals, and thus varying and inadequate measurement of the flux of the chemical signal. The present invention provides an electrode that is capable of detecting the electrochemical signal at very low levels in a manner that allows for direct, accurate correlation between the amount of signal generated and the amount of the molecule (e.g., glucose) in the area from which it is moved (e.g., in the human subject).

The invention is remarkable in that it allows for the noninvasive detection and measuring of amounts of a biomedically relevant compound, e.g., glucose, at levels are 1, 2, or even 3 orders of magnitude less than the concentration of that compound in, for example, blood. For example, glucose might be present in blood in a concentration of about 5 millimolar. However, the concentration of glucose in a hydrogel patch which withdraws glucose through skin as described in the system above is on the order of 2 to 100 micromolar. Micromolar amounts are 3 orders of magnitude less than millimolar amounts. The ability to accurately and quickly detect glucose in such small concentrations is attained by constructing the working electrode with the mask and other components described herein.

EXAMPLES

The following examples are put forth so as to provide those of ordinary skill in the art with a complete disclosure and description of how to make and use various specific assemblies of the present invention and are not intended to limit the scope of what the inventors regard as their invention. The data presented in these examples are computer-simulated (i.e., the data is generated from a computer model of the mask and electrode assembly described herein). The computer model of the invention uses the following parameters:

glucose diffusivity: $1.3 \times 10^{-6}$ cm$^2$/sec;
peroxide diffusivity: $1.2 \times 10^{-5}$ cm$^2$/sec;
enzyme rate constant: 735 sec$^{-1}$;
$K_M$ for glucose: $1.1 \times 10^5$ nmol/ml;
$K_M$ for glucose: 200 nmol/ml;
initial oxygen concentration: 240 nmol/ml;
enzyme loading in gel: 100 U/ml; and
glucose flux: 5 nmol/cm$^2$ hr.

Efforts have been made to ensure accuracy with respect to numbers used, (e.g., amounts, particular components, etc.) but some deviations should be accounted for. Unless indicated otherwise, parts are parts by weight, surface area is geometric surface area, temperature is in degrees centigrade, and pressure is at or near atmospheric pressure.

EXAMPLE 1

(glucose monitoring device—no mask)

The peroxide flux or current error at the surface of a platinum working electrode in a glucose monitoring device comprising an iontophoresis electrode/platinum working electrode/hydrogel assembly (no mask) was simulated by computer. The computer-based experiments were designed to simulate the use of the device in vivo (e.g., the manner in which the device is used to monitor glucose in a human subject). The computer simulation was based upon a continuous glucose flux into the hydrogel (5 nmol/cm$^2$ hr), 18 U/ml glucose oxidase loaded into the gel, a gel thickness of 600 microns, and alternate intervals of: 1) iontophoresis (i.e., the iontophoresis electrodes are activated, and glucose molecules are electrically drawn through the subject's skin and into and through the hydrogel patch); and 2) detection of an electrical current at the working electrode (i.e., the iontophoresis electrode is switched off and the sensing unit to detect electrical current at the working electrode is on). The experimental protocol is shown in Table 1.

TABLE 1

Experimental Protocol for Computer Simulation

| Interval No. | Interval Length (min) | Iontophoresis Electrode | Working Electrode |
|---|---|---|---|
| 1 | 15 | on | off |
| 2 | 5 | off | on |
| 3 | 15 | on | off |
| 4 | 5 | off | on |
| 5 | 15 | on | off |
| 6 | 5 | off | on |

Figure 7:
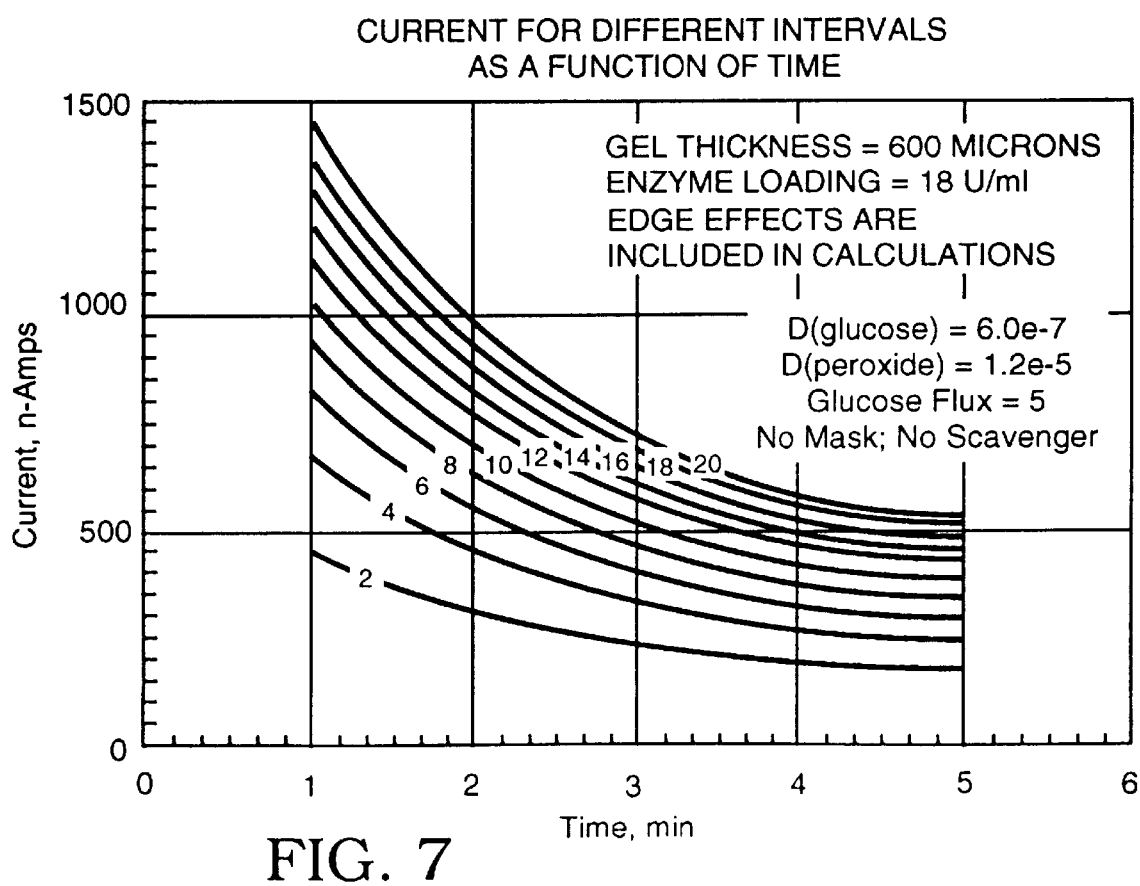
FIG. 7 is a graph showing the measured electrical current at the working electrode in the absence of the mask for different intervals as a function of time.

This protocol was repeated for a total of 20 intervals. The results of the computer model are shown in FIG. 7.

These data indicate that the electrical current measured at the working electrode is a function of the interval number, i.e., peroxide flux at the working electrode increases with increasing interval number. This is a direct result of the accumulation of hydrogen peroxide at the periphery of the working electrode as a result of radial transport of hydrogen peroxide within the gel toward the electrode. As a result, the device is never able to provide a steady state measurement profile in the presence of a continuous flow of glucose and hydrogen peroxide.

EXAMPLE 2 with a mask

The computer model described in Example 1 was repeated with the same parameters, except that the device included a mask of the invention positioned between the subject's skin and the hydrogel. The position of the mask allows transport of glucose toward the working electrode only in a direction that is substantially axial to the catalytic face of the working electrode, and thus production of hydrogen peroxide only in a region of the hydrogel that is directly beneath the working electrode. Therefore, the amount of hydrogen peroxide that is produced at a position outside the perimeter of the working electrode is essentially eliminated.

Figure 8:
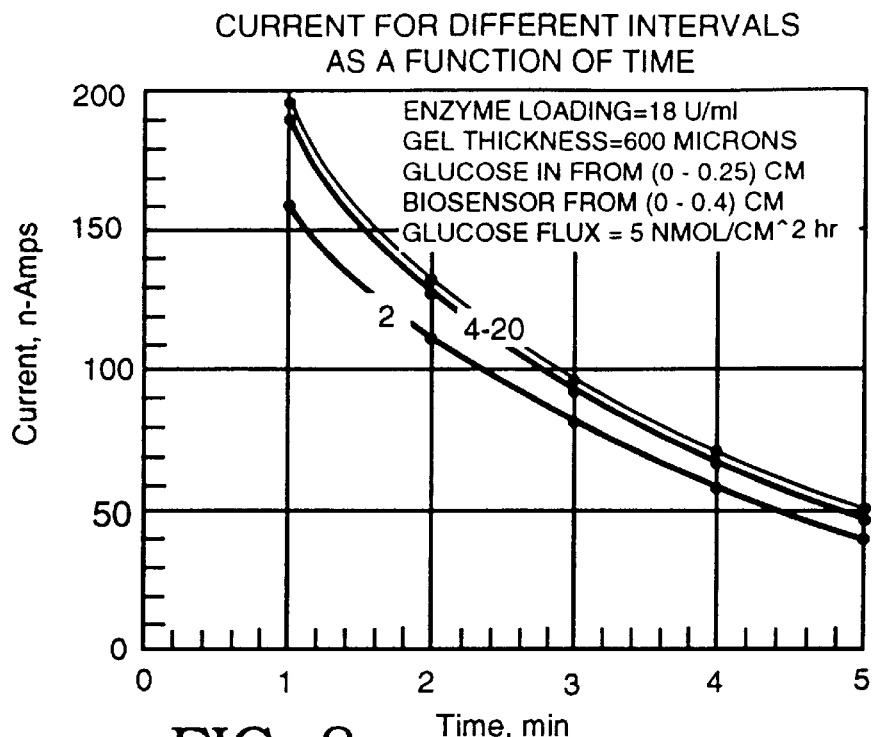
FIG. 8 is a graph showing the measured electrical current at the working electrode in the presence of the mask for different intervals as a function of time.

The results of the computer model, expressed as the measured electrical current as a function of interval number, are shown in FIG. 8. These data indicate that after interval 2, the is independent of interval number. Thus, within only 2 to 4 intervals, the device provides a steady state profile of the measurement of a continuous flux of hydrogen peroxide.

EXAMPLE 3 with and without a mask

Figure 9:
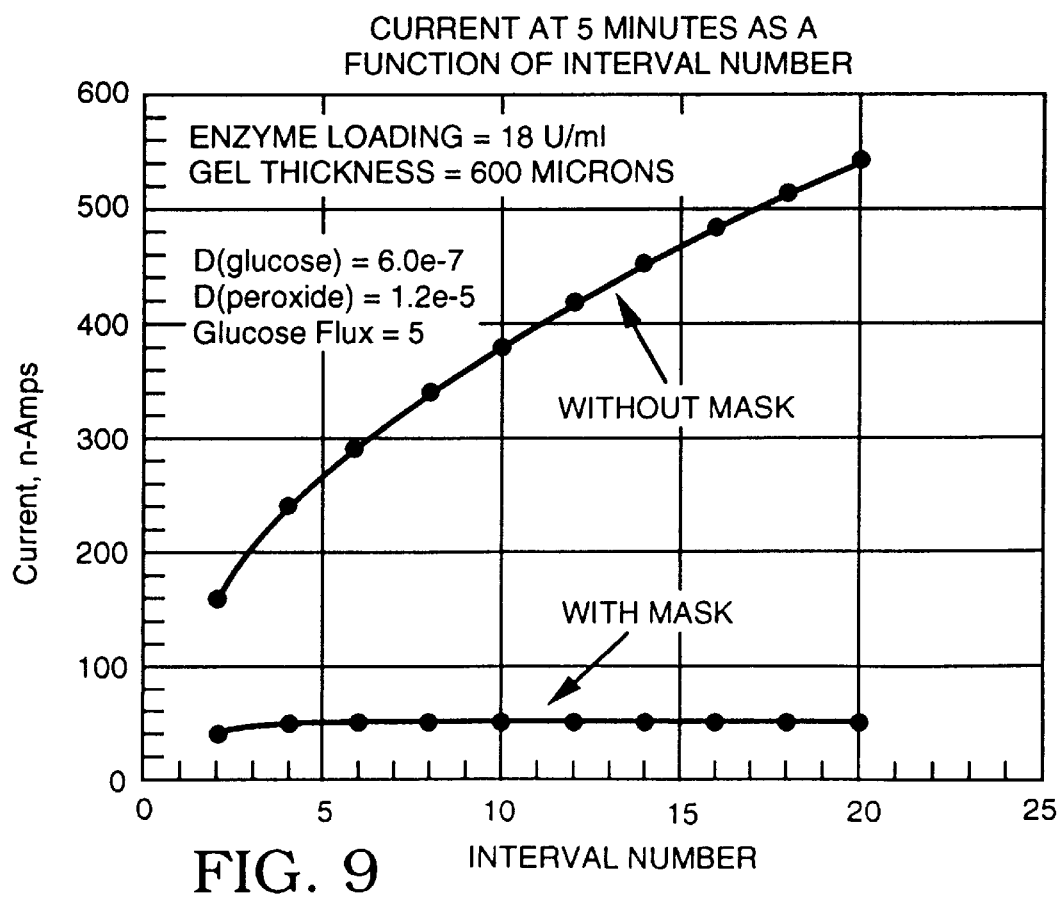
FIG. 9 is a graph showing a comparison of the measured electrical current at the working electrode either with the mask or without the mask as a function of interval number.

The data from the computer simulations of measurement of a constant glucose flux (5 nmol/cm$^2$ hr) using a glucose monitoring device without the mask (Example 1) and with the mask (Example 2) were analyzed to plot the electrical current measured at the working electrode after 5 minutes of measurement versus the interval number (FIG. 9). This analysis shows that in the absence of the mask, there is a strong dependence of the measured electrical current on the interval number. When the mask of the invention is included in the device, the profile of the measured electrical current is essentially linear, and thus independent of interval number (see "with mask" line of FIG. 9).

The instant invention is shown and described herein in what is considered to be the most practical, and preferred embodiments. It is recognized, however, that departures may be made therefrom which are within the scope of the invention, and that modifications will occur to one skilled in the art upon reading this disclosure.

What is claimed is:

1. A method of measuring a concentration of a chemical present in a bloodstream of a mammalian subject, comprising the steps of:

contacting a mammalian subject's skin with a sensor assembly comprising;

a) an ionically conductive material in contact with the skin;

b) a working electrode in contact with the ionically conductive material the working electrode having a catalytic surface; and c) a mask having an opening therein wherein the mask is positioned between the skin and the working electrode;

transporting a chemical through the skin and ionically conductive material whereby the mask blocks flow to the catalytic surface except for flow substantially axial to the catalytic surface;

monitoring an electrical signal generated at the working electrode by catalytic conversion into an electric signal at the catalytic surface of the working electrode;

wherein the electrical signal generated at the working electrode over a given period of time is correlated with a concentration of chemical present in the bloodstream of the mammalian subject.

2. The method of claim 1, wherein the assembly further comprises:

d) an electroosmotic electrode in contact with the ionically conductive material and said transporting is accomplished by applying an electrical current to the electroosmotic electrode.

3. The method of claim 1, wherein the chemical is glucose, the ionically conductive material is a hydrogel, and the catalytic surface of the working electrode comprises a material selected from the group consisting of platinum oxide and platinum dioxide.

4. The method of claim 3, wherein the hydrogel comprises a hydrophilic polymer, water and glucose oxidase.

5. The method of claim 4, wherein the mammalian subject is a human.

6. The method of claim 1, wherein the mammalian subject is a human.

7. The method of claim 1, wherein the chemical is glucose.

8. The method of claim 1, wherein the ionically conductive material comprises glucose oxidase.

9. The method of claim 1, wherein the catalytic surface of the working electrode is comprised of a material selected from the group consisting of platinum oxide and platinum dioxide.

10. The method of claim 1, wherein the mammalian subject is a human, the chemical is glucose, the ionically conductive material comprises glucose oxidase, and the surface of the working electrode is comprised of a material selected from the group consisting of platinum oxide and platinum dioxide.

11. A method of measuring a glucose concentration in a mammalian subject, comprising:

contacting a first surface of an ionically conductive material with a skin surface wherein the ionically conductive material comprises water and glucose oxidase;

contacting a second surface of the conductive material with a working electrode;

applying current to the skin in an amount sufficient to draw glucose into the conductive material whereby the glucose is converted to gluconic acid and hydrogen peroxide and the hydrogen peroxide is drawn to the working electrode; and positioning a mask impermeable to the hydrogen peroxide between the skin surface and a surface of the working electrode so as to shield the working electrode surface from hydrogen peroxide moving to the working electrode surface via any path other than a path substantially axial to the working electrode surface.

12. The method of claim 11, wherein the mammalian subject is a human.

13. The method of claim 11, wherein the working electrode is comprised of a material selected from the group consisting of platinum oxide and platinum dioxide.

* * * * *